US00PP13538P2

(12) United States Plant Patent
de Jong

(10) Patent No.: US PP13,538 P2
(45) Date of Patent: Feb. 4, 2003

(54) HYPERICUM PLANT NAMED 'KOLMAGIF'

(75) Inventor: Jan de Jong, Heelsum (NL)

(73) Assignee: Gebr. Kolster B.V., Boskoop (NL)

( * ) Notice: Subject to any disclaimer, the term of this patent is extended or adjusted under 35 U.S.C. 154(b) by 0 days.

(21) Appl. No.: 10/006,806

(22) Filed: Dec. 5, 2001

(51) Int. Cl.[7] ..... A01H 5/00
(52) U.S. Cl. ..... Plt./226

(58) Field of Search ..... Plt./226

*Primary Examiner*—Bruce R. Campell
*Assistant Examiner*—Annette Para
(74) *Attorney, Agent, or Firm*—C. A. Whealy

(57) ABSTRACT

A new and distinct cultivar of Hypericum plant named 'Kolmagif', characterized by its upright and outwardly spreading plant habit; dark green leaves; bright red-colored fruits; good postproduction longevity; and resistance to rust pathogens.

2 Drawing Sheets

BOTANICAL CLASSIFICATION/CULTIVAR DESIGNATION

*Hypericum inodorum* cultivar Kolmagif.

BACKGROUND OF THE INVENTION

The present Invention relates to a new and distinct cultivar of Hypericum plant, botanically known as *Hypericum inodorum*, commercially used as cut stems with fruits, and hereinafter referred to by the name 'Kolmagif'.

The new Hypericum is a product of a planned breeding program conducted by the Inventor in Wageningen, The Netherlands. The objective of the breeding program was to develop cut Hypericum varieties with attractive fruit coloration.

The new cultivar originated from a cross made by the Inventor in 1998 of two unidentified proprietary seedling selections, not patented. The cultivar Kolmagif was discovered and selected by the Inventor in 2000 as a flowering plant within the progeny of the stated cross in a controlled environment in Wageningen, The Netherlands.

Asexual reproduction of the new Hypericum by terminal cuttings taken at Boskoop, The Netherlands, has shown that the unique features of this new Hypericum are stable and reproduced true to type in successive generations of asexual reproduction.

SUMMARY OF THE INVENTION

The following traits have been repeatedly observed and are determined to be the unique characteristics of 'Kolmagif'. These characteristics in combination distinguish 'Kolmagif' as a new and distinct cultivar:

1. Upright and outwardly spreading plant habit.
2. Dark green leaves.
3. Bright red-colored fruits.
4. Good postproduction longevity.
5. Resistance to rust pathogens.

Plants of the new Hypericum differ from plants of the parent seedling selections primarily in fruit coloration.

Plants of the new Hypericum can be compared to plants of the Hypericum cultivar Excellent Flair, not patented. In side-by-side comparisons conducted in Boskoop, The Netherlands, plants of the new Hypericum differed from plants of the cultivar Excellent Flair in the following characteristics:

1. Plant of the new Hypericum had darker green-colored leaves than plants of the cultivar Excellent Flair.
2. Leaves of plants of the new Hypericum did not sunburn whereas leaves of plants of the cultivar Excellent Flair sunburned.
3. Fruits of plants of the new Hypericum were bright red in color whereas fruits of plants of the cultivar Excellent Flair were red brown in color.

BRIEF DESCRIPTION OF THE PHOTOGRAPHS

The accompanying colored photographs illustrate the overall appearance of the new Hypericum, showing the colors as true as it is reasonably possible to obtain in colored reproductions of this type. Colors in the photographs may differ slightly from the color values cited in the detailed botanical description which accurately describe the colors of the new Hypericum.

The photograph on the first sheet comprises a side perspective view of a typical plant of 'Kolmagif'.

The photographs on the second sheet (top to bottom) are close-up views of typical upper surfaces of developing and fully expanded leaves of 'Kolmagif', a typical opened flower of 'Kolmagif', and typical fruits of 'Kolmagif'.

DETAILED BOTANICAL DESCRIPTION

The new Hypericum has not been observed under all possible environmental conditions. The phenotype may vary somewhat with variations in environment such as temperature, daylength and light intensity, without, however, any variance in genotype.

The aforementioned photographs, following observations and measurements describe plants grown in Boskoop, The Netherlands, in an outdoor nursery and under commercial production practices. Plants were about two years old. The photographs and description were taken during the summer when outdoor day temperatures ranged from 14 to 27° C. and day temperatures ranged from 7 to 14° C. In the following description, color references are made to The Royal Horticultural Society Colour Chart, 2001 Edition, except where general terms of ordinary dictionary significance are used.

Botanical classification: *Hypericum inodorum* cultivar Kolmagif.

Parentage:

*Female parent.*—Unidentified proprietary selection of *Hypericum inodorum*, not patented.

*Male parent.*—Unidentified proprietary selection of *Hypericum inodorum*, not patented.

Propagation:

*Type.*—Terminal cuttings.

*Time to produce a rooted cutting.*—About 30 days at 20° C.

*Root description.*—Freely branching; medium thickness; brownish green in color.

Plant description:

*Plant form.*—Upright and outwardly spreading perennial woody shrub; globular.

*Growth habit.*—Moderately vigorous. Freely branching; dense and bushy growth habit.

*Plant height.*—About 60 cm.

*Plant width* (*spread*).—About 80 cm.

*Quantity of stems per year.*—About 13.

*Lateral branches.*—Length: About 13 cm. Diameter: About 2.5 mm. Internode length: About 3.3 cm. Strength: Moderate. Texture: Smooth. Color: N144A; overlain with slight anthocyanin, 181C.

*Foliage description.*—Leaves opposite; single; sessile and generally symmetrical. Length: About 5.5 cm. Width: About 2.7 cm. Shape: Ovate. Apex: Acute to obtuse. Base: Obtuse. Margin: Entire Texture: Glabrous; slightly rugose. Venation pattern: Pinnate. Color: Developing leaves, upper surface: 141A. Developing leaves, lower surface: 138B. Fully expanded leaves, upper surface: Between 139A and 137A. Fully expanded leaves, lower surface: 138B. Venation, upper surface: 144C. Venation, lower surface: 144D.

Flower description:

*Flower type and habit.*—Bright yellow single flowers arranged in terminal compound umbels with about six flowers per umbel; about 16 flowers and flower buds per lateral branch. Flowers not fragrant. Flowers not persistent. Flowers upright.

*Natural flowering season.*—Summer, typically July and August in Boskoop, The Netherlands; flowering period typically lasts about 60 days.

*Postproduction longevity.*—Cut stems are typically harvested when all flowers have developed fruits. Postproduction longevity of cut stems with fruits is about two weeks.

*Inflorescence height.*—About 3.4 cm.

*Inflorescence diameter.*—About 6 cm.

*Flower buds.*—Height: About 7 mm. Diameter: About 6 mm. Shape: Broadly elliptic. Color: Base and mid-section, 13A; apex, 28B.

*Flowers.*—Diameter: About 2.9 cm. Depth: About 2 cm.

*Petals.*—Quantity per flower: Five. Length: About 1.5 cm. Width: About 9 mm. Shape: Broadly elliptic to obovate. Aspect: Slightly concave. Apex: Acute. Base: Attenuate. Margin: Entire. Texture, upper and lower surfaces: Smooth. Color: Developing and fully expanded petals, upper surface: 13A; color does not fade with subsequent development. Developing and fully expanded petals, lower surface: 12A to 13A.

*Sepals.*—Quantity per flower: Five. Length: About 9 mm. Width: About 7 mm. Shape: Broadly elliptic to broadly ovate. Aspect: Convex. Apex: Acute to obtuse. Base: Broadly cuneate. Margin: Entire. Texture, upper and lower surfaces: Smooth. Color: Developing sepals, upper surface: 143B; at margin, 178A to 178B. Developing sepals, lower surface: 138B; tinted with anthocyanin, 178B; at margin, 178B. Fully expanded sepals, upper surface: 143A. Fully expanded sepals, lower surface: 143C.

*Peduncles.*—Length: About 1 cm. Diameter: About 1 mm. Orientation: Erect to about 10° from vertical. Strength: Moderately strong. Color: 144A; overlain with anthocyanin, 178B.

*Pedicels.*—Length: About 1 cm. Diameter: About 1 mm. Orientation: Erect to about 60° from vertical. Strength: Moderately strong. Color: 138C; overlain with anthocyanin, 178A.

*Reproductive organs.*—Stamens: Quantity per flower: About 85. Anther shape: Broadly ovate. Anther length: About 0.5 mm. Anther color: 178B to 178C. Pollen amount: Moderate. Pollen color: 12A to 13B. Pistils: Quantity per flower: Three. Pistil length: About 6 mm. Stigma shape: Globular. Stigma color: Close to 34D. Style length: About 5.9 mm. Style color: 154D. Ovary color: 154C to 154D.

*Fruits.*—Quantity per flower: One. Days to ripening: About 25. Longevity on the plant: About 30 days. Type: Capsule. Shape: Ellipsoidal. Length: About 1.1 cm. Diameter: About 9 mm. Texture: Smooth, glabrous. Color: 50A to 50B, on a cream-colored, close to 11D, background, most noticeable at the base.

*Seeds.*—Quantity per fruit: More than 100. Length: About 0.8 mm. Diameter: About 0.5 mm. Texture: Smooth, glabrous. Color: 199A to N199A.

Disease resistance: Plants of the new Hypericum have been observed to be resistant to rust pathogens common to Hypericum.

Temperature tolerance: Plants of the new Hypericum have been observed to tolerate temperatures ranging from −15 to 35° C.

It is claimed:

1. A new and distinct cultivar of Hypericum plant named 'Kolmagif', as illustrated and described.

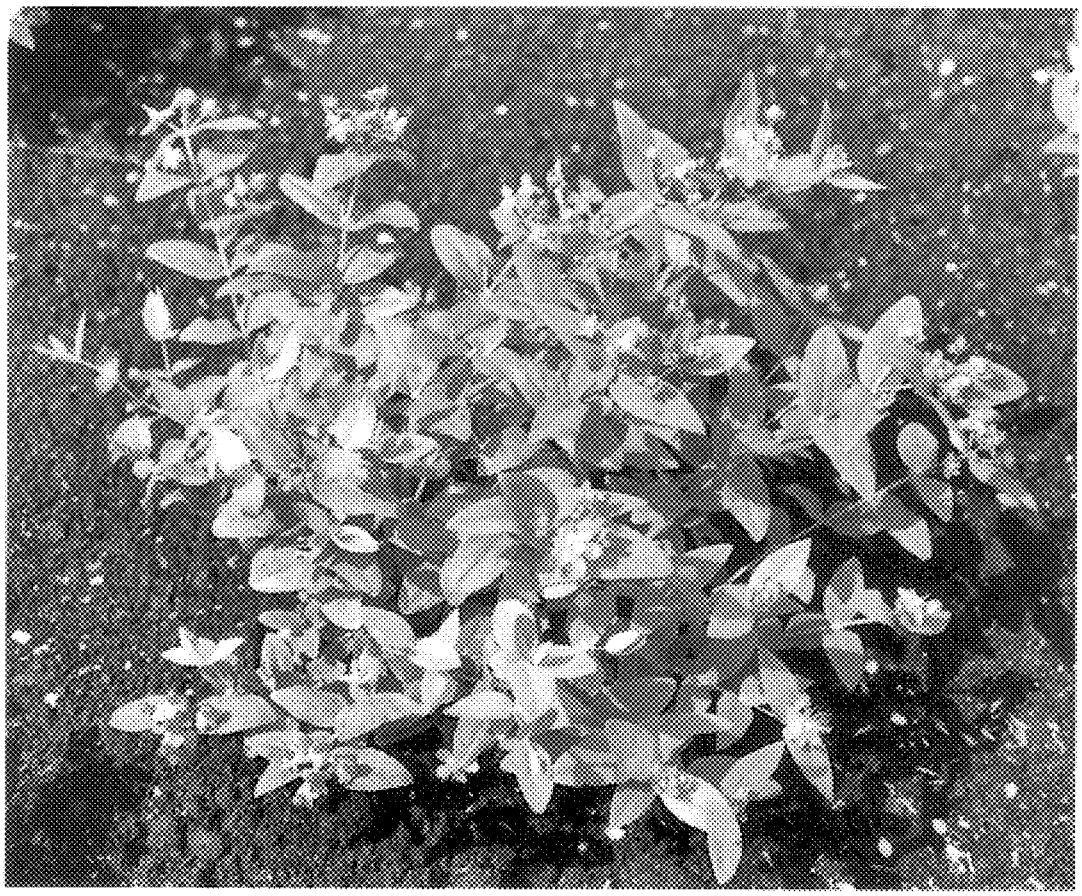

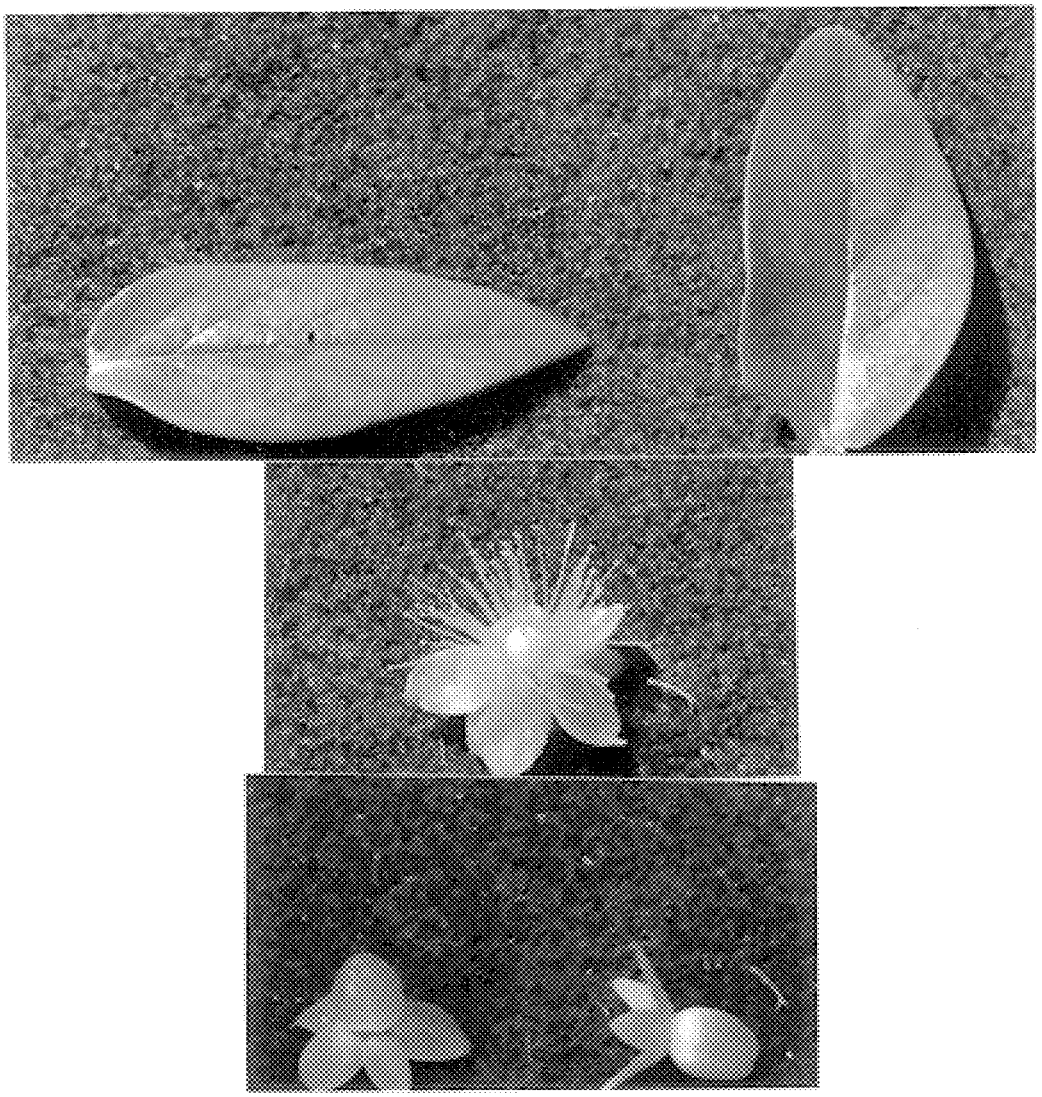

* * * * *